United States Patent [19]
Dutton et al.

[11] Patent Number: 5,883,080
[45] Date of Patent: Mar. 16, 1999

[54] ANTIPARASTIC AUERMECTIN DERIVATIVES

[75] Inventors: Christopher James Dutton; Stephen Paul Gibson; Michael John Witty, all of Sandwich, United Kingdom

[73] Assignee: Pfizer Inc., New York, N.Y.

[21] Appl. No.: 8,238

[22] Filed: Jan. 16, 1998

Related U.S. Application Data

[63] Continuation of Ser. No. 591,534, filed as PCT/EP94/02433, Jul. 22, 1994, abandoned.

[30] Foreign Application Priority Data

Aug. 4, 1993 [GB] United Kingdom ............ 9316129

[51] Int. Cl.$^6$ .................... A61K 31/70; C07H 17/08; A01N 43/90
[52] U.S. Cl. ............... 514/50; 514/450; 536/7.1; 549/264
[58] Field of Search ............ 549/264; 514/450, 514/30; 536/7.1

[56] References Cited

U.S. PATENT DOCUMENTS 5,411,946  5/1995  Newbold et al. ................ 514/30
5,516,761  5/1996  Choi et al. ................ 514/30

FOREIGN PATENT DOCUMENTS 62-252788  11/1987  Japan .

OTHER PUBLICATIONS

Andrew Streifwieser, Jr. and Clayton H. Heathcock, "Introduction to Organic Chemistry", 3rd Edition, Macmillan Publishing Company, New York, 1985, pp. 396–398.

*Primary Examiner*—Laura L. Stockton
*Attorney, Agent, or Firm*—Peter C. Richardson; Gregg C. Benson; Robert T. Ronau

[57] ABSTRACT

Antiparasitic avermectin derivatives of formula (I), where the broken line represents an optional bond, $R^1$ and $R^4$ are independently H, OH, halo, oximino, or an organic radical, $R^2$, $R^6$ and $R^7$ are organic radicals and $R^3$ is alpha-oleandrosyl or 4'-(alpha-oleandrosyl)-alpha-oleandrosyl optionally substituted at the 4'- or 4"-position, and $R^{12}$ and $R^{13}$ are independently H, CN, $CONH_2$, $C_1$–$C_8$ alkyl or aryl optionally substituted with at least one halo, OH, $C_1$–$C_8$ alkylthio group.

13 Claims, No Drawings

ANTIPARASTIC AUERMECTIN DERIVATIVES

This application is a continuation of application Ser. No. 08/591,534, filed on Jan. 25, 1996, now adandoned entitled "Antiparasitic Agents", -which is the national stage of PCT Application No. EP 94/02433, filed on Jul. 22, 1994.

This invention relates to antiparasitic agents and in particular to compounds related to the avermectins and milbemycins but having an alkylidene substituent at the 5-position.

The avermectins are a group of broad-spectrum antiparasitic agents referred to previously as the C-076 compounds They are produced by fermenting a certain strain of micro-organism *Streptomyces avermitilis* in an aqueous nutrient medium. The preparation and structure of these compounds obtained by fermentation are described in British Patent Specification 1573955. The milbemycins are structurally related macrolide antibiotics lacking the sugar residues at the 13-position. They may be produced by fermentation, for example as described in British Patent Specification No. 1390336 and European Patent Specification No. 0170006.

Compounds related to the original C-076 avermectins have also been prepared by fermentation of avermectin-producing micro-organisms. For example European Patent Specifications 0214731 and 0317148 describe production of compounds related to the C-076 avermectins but having a different substituent at the 25-position by fermentation in the presence, in the fermentation medium, of certain acids.

In addition to these fermentation-derived products, a large number of publications describe compounds derived semisynthetically from these products, many of which possess useful antiparasitic properties. Some of this chemistry is reviewed in *Macrolide Antibiotics*, Omura S., Ed., Academic Press, New York (1984) and by Davies, H. G. and Green, R. H. in *Natural Product Reports* (1986), 3, 87–121 and in *Chem Soc Rev* (1991), 20, 211–269 and 271–239.

Other publications mentioning different combinations of substituents at various positions on the avermectin or milbemycin nucleus are EP-A-317148, 340932, 355541, 350187, 410165, 259779 and 254583; DE-A-2329486 and GB-A-2166436.

No avermectin derivatives having an alkylidene substituent at the 5-position are known, neither has any process capable of producing such compounds been reported. Japanese Patent Application No. 86-94754 (published under No. 87-252788) of Sankyo describes milbemycins and aglycone derivatives having a methylidene substituent at the 5-position, but the processes described for making them cannot be used for making similarly substituted avermectins or avermectin monosaccharides, as saccharide groups are removed by hydrolysis under the acidic conditions used.

It has now been discovered that avermectin derivatives and their monosaccharides having an alkylidene substituent at the 5-position may be prepared and that certain of these compounds have unexpected antiparasitic properties, in particular high potency against important arthropod parasites of cats and dogs. In addition, they have improved safety in mammals compared to previously known avermectins.

According to one aspect of the invention, there are provided compounds of formula (I) having antiparasitic activity

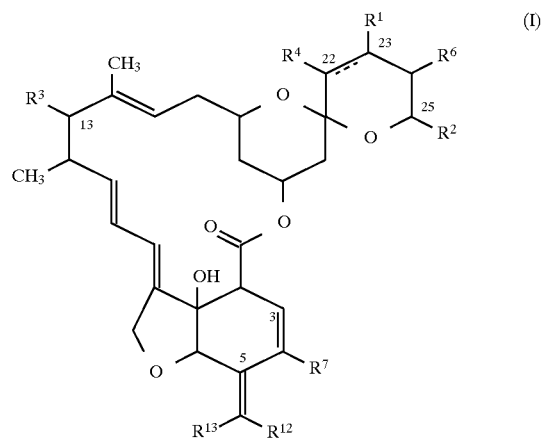

wherein the broken line represents an optional bond, $R^1$ and $R^4$ being absent when this bond is present, $R^1$ and $R^4$ are independently H or $OR^{14}$ where $R^{14}$ is H, $C_1$–$C_8$ alkyl, $C_2$–$C_8$ alkenyl, aralkyl, $C_2$–$C_8$ alkanoyl, $C_3$–$C_8$ alkenoyl, aralkanoyl, aroyl or carbamoyl;

$R^2$ is:
(a) an alpha-branched $C_3$–$C_8$ alkyl, alkenyl, alkoxyalkyl, or alkylthioalkyl group; and alpha-branched $C_4$–$C_8$ alkynyl group; a ($C_5$–$C_8$)cycloalkyl-alkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methylene or one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or
(b) a group of the formula —$CH_2R^8$ wherein $R^8$ is H, $C_1$–$C_8$ alkyl, $C_2$–$C_8$ alkenyl, $C_2$–$C_8$ alkynyl, alkoxyalkyl or alkylthioalkyl containing from 1 to 6 carbon atoms in each alkyl or alkoxy group, wherein any of said alkyl, alkoxy, alkenyl or alkynyl groups may be substituted by one or more halo atoms; or $R^8$ is a $C_3$–$C_8$ cycloalkyl or $C_5$–$C_8$ cyoloalkenyl group, either of which may optionally be substituted by methylene or one or more $C_1$–$C_4$ alkyl groups or halo atoms; or $R^8$ is a 3 to 6 membered oxygen or sulphur containing heterocyclic ring which may be saturated, or fully or partially unsaturated and which may optionally be substituted by one or more $C_1$–$C_4$ alkyl groups or halo atoms; or $R^8$ is a group of the formula $SR^9$ wherein $R^9$ is $C_1$–$C_8$ alkyl, $C_2$–$C_8$ alkenyl, $C_3$–$C_8$ alkynyl, $C_3$–$C_8$ cycloalkyl, $C_5$–$C_8$ cycloalkenyl, phenyl or substituted phenyl wherein the substituent is $C_1$–$C_4$ alkyl, $C_1$–$C_4$ alkoxy or halo; or $R^8$ is a 3 to 6 membered oxygen or sulphur containing heterocyclic ring which may be saturated, or fully or partially unsaturated and which may optionally be substituted by one or more $C_1$–$C_4$ alkyl groups or halo atoms; or
(c) a $C_1$–$C_6$ alkyl group substituted by one oxo or one or more hydroxy groups or by a single oxygen atom on two adjacent carbon atoms forming an oxirane ring, or $R^2$ is a $C_1$–$C_5$ alkyl group substituted by a ($C_1$–$C_6$) alkoxy-carbonyl group, said substituents on $R_2$ being attached to either or both of a terminal carbon atom and a carbon atom adjacent a terminal carbon atom of $R^2$; or (d) =CH$_2$ or a group of the formula:

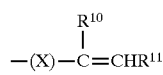

wherein R$^{10}$ and R$^{11}$ are both H; R$^{10}$ is H and R$^{11}$ is C$_1$–C$_3$ alkyl, or one of R$^{10}$ and R$^{11}$ is H and the other is phenyl, heteroaryl, C$_2$–C$_6$ alkoxycarbonyl or substituted phenyl or heteroaryl wherein said substituent is fluorine, chlorine, C$_1$–C$_4$ alkyl, C$_1$–C$_4$ alkoxy, C$_1$–C$_4$ alkylthio, hydroxy(C$_1$–C$_4$)alkyl, cyano, aminosulphonyl, C$_2$–C$_6$ alkanoyl, C$_2$–C$_6$ alkoxycarbonyl, nitro, trifluoromethyl, trifluoromethoxy, amino or mono or di(C$_1$–C$_4$) alkylamino; and X is a direct bond or is an alkylene group having from 2 to 6 carbon atoms which may be straight or branched-chain; or (e) phenyl which may optionally be substituted with at least one substituent selected from C$_1$–C$_4$ alkyl, C$_1$–C$_4$ alkylthio groups, halo atoms, trifluoromethyl, and cyano;

or R$^2$ may be a group of formula (II):

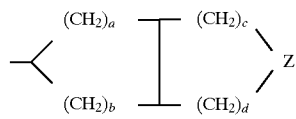

wherein Z is O, S or —CH$_2$— and a, b, c and d may each independently be 0, 1 or 2, the sum of a, b, c and d not exceeding 5;

R$^6$ is H or C$_1$–C$_6$ alkyl;

R$^7$ is CH$_3$, —CH$_2$—OR$^{14}$ where R$^{14}$ is as defined above, or —CH$_2$X where X is a halogen atom; and R$^3$ is a group of formula:

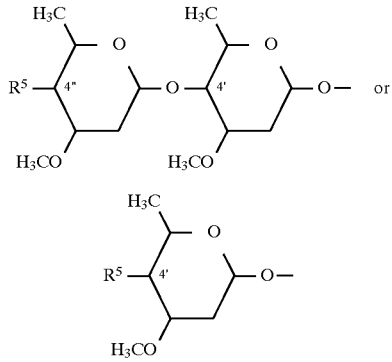

wherein R$^5$ is attached to C-4" or C-4' by a single bond and is hydrogen, halo, hydroxy, C$_1$–C$_9$ alkanoyloxy or alkenoyloxy, aroyloxy, C$_1$–C$_8$ alkoxy, amino, N-(C$_1$–C$_8$) alkylamino, N,N-di(C$_1$–C$_9$)-alkylamino, N-(C$_1$–C$_9$) alkanoylamino, or N,N-di(C$_1$–C$_9$)alkanoylamino;

or R$^5$ is attached to C-4" or C-4' by a double bond and is oxo, optionally substituted oximino, semicarbazido, N-(C$_1$–C$_4$)alkylsemicarbazono, N,N-di(C$_1$–C$_4$) alkylsemicarbazono, (C$_1$–C$_4$)alkylbenzoylhydrazono, and R$^{12}$ and R$^{13}$ are independently H, CN, CONH$_2$, C$_1$–C$_6$ alkyl or aryl optionally substituted with at least one halo, OH, C$_1$–C$_6$ alkoxy or C$_1$–C$_6$ alkylthio group.

In all the above definitions, unless the context requires otherwise, alkyl groups containing 3 or more carbon atoms may be straight or branched-chain; halo means fluoro, chloro, bromo or iodo; and aryl means phenyl optionally substituted by one or more C$_1$–C$_4$ alkoxy groups or halo atoms.

Compounds within the scope of the invention include 5-cyanomethylidene-25-cyclohexyl avermectin B2;
5-carbamoylmethylidene-25-cyclohexyl avermectin B2;
5-cyanomethylidene-22,23-dihydroavermectin B1a monosaccharide;
5-methylidene-22,23-dihydroavermectin B1a monosaccharide;
5-methylidene-25-cyclohexyl-22,23-dihydroavermectin B1 monosaccharide;
5-methylidene-25-cyclohexylavermectin B2;
and 5-ethylidene-25-cyclohexylavermectin B2.

The compounds of formula (I) may be prepared from a compound of formula (II):

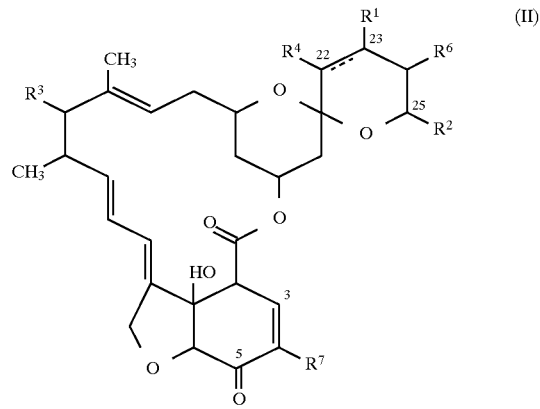

wherein R$^1$, R$^2$, R$^3$, R$^4$, R$^6$ and R$^7$ are as defined above. The compounds of formula (II) may generally be prepared by oxidation of the corresponding 5-hydroxy compound, for example using manganese dioxide, groups R$^1$–R$^7$ being protected by conventional methods if necessary. These 5-hydroxy analogues may themselves be prepared by methods known in the art.

The addition of a phosphorus ylide of the formula R$^{13}$R$^{12}$C=PPh$_3$ to a compound of the formula (II) at low temperature (–100° C. to 0° C.) in an inert organic solvent such as tetrahydrofuran produces a compound of formula (I). The phosphorus ylide may be prepared using known methods from a compound of formula R$^{13}$R$^{12}$CH⊕PPh$_3$X⊖, where X⊖ is a halide ion, in the presence of base. Alternatively a compound of formula R$^{13}$R$^{12}$CHP(O)(OR$^{15}$)$_2$, where R$^{15}$ is an alkyl group, may firstly be treated with a base, then added to a compound of formula (II), to produce a compound of formula (I). This reaction may also be performed in a two-phase mixture of a chlorinated organic solvent and aqueous alkali containing a compound of formula R$^{13}$R$^{12}$CHP(O)(OR$^{15}$)$_2$ and a phase-transfer reagent and a compound of formula (II), to form a compound of formula (I).

When it is desired to prepare a compound in which R$^{12}$ or R$^{13}$ is carbamoyl, a phosphorus ylide in which R$^{12}$ or R$^{13}$ is cyano may be used to obtain a cyanomethylidene derivative of formula (I) which may be hydrolysed under mild conditions, for example in the presence of manganese dioxide in methylene chloride at ambient temperature.

The compounds of the invention are effective in treating a variety of conditions caused by endoparasites including, in particular, helminthiasis which is most frequently caused by a group of parasitic worms described as nematodes and which can cause severe economic losses in swine, sheep, horses and cattle as well as affecting domestic animals and poultry. The compounds are also effective against other nematodes which affect humans and various species of animals including, for example, Dirofilaria in dogs and various parasites which can infect animals and humans including gastro-intestinal parasites such as Ancylostoma, Necator, Ascaris, Strongyloides, Trichinella, Toxocara, Capilaria, Trichuris, Enterobius and parasites which are found in the blood or other tissues and organs such as filiarial worms and the extra-intestinal stages of Strongyloldes, Trichinella and Toxocara.

The compounds are also of value in treating ectoparasite infectins including in particular arthropod ectoparasites such as fleas, ticks, mites, lice, blowfly and biting Insects and migrating dipterous larvae which can affect cattle and horses.

The compounds are also insecticides active against household pests such as the cockroach, clothes moth, carpet beetle and the housefly as well as being useful against arthropod pests of stored grain and of agricultural plants such as spider mites, aphids, caterpillars and against migratory orthopterans such as locusts. We have discovered that certain compounds within the scope of this invention have unexpectedly high potent activity against important arthropod parasites of cats and dogs.

The compounds of formula (I) may be administered as a formulation appropriate to the specific use envisaged and to the particular species of host animal being treated and the parasite or insect involved. For use as an anthelmintic the compounds may be administered by injection, either subcutaneously or intramuscularly, alternatively they may be administered orally in the form of a capsule, bolus, tablet, chewable tablet or liquid drench, or they may be administered as a topical formulation or as an implant. For topical application dip, spray, powder, dust, pour-on, spot-on, jetting fluid, shampoos, collar, tag or harness may be used. Such formulations are prepared in a conventional manner in accordance with standard veterinary practice. Thus capsules, boluses or tablets may be prepared by mixing the active ingredient with a suitable finely divided diluent or carrier, additionally containing a disintegrating agent and/or binder such as starch, lactose, talc, or magnesium stearate. A drench formulation may be prepared by dispersing the active ingredient in an aqueous solution together with dispersing or wetting agents and injectable formulations may be prepared in the form of a sterile solution or emulsion. Pour-on or spot-on formulations may be prepared by dissolving the active ingredient in an acceptable liquid carrier vehicle, such as butyl digol, liquid paraffin or non-volatile ester with or without addition of a volatile component such as isopropanol. Alternatively, pour-on, spot-on or spray formulations can be prepared by encapsulation to leave a residue of active agent on the surface of the animal. These formulations will vary with regard to the weight of active compound depending on the species of host animal to be treated, the severity and type of infection and the body weight of the host. Generally for oral parenteral and pour-on administration a dose of from about 0.001 to 10mg per g of animal body weight given as a single dose or in divided doses for a period of from 1 to 5 days will be satisfactory but of course there can be instances where higher or lower dosage ranges are indicated and such are within the scope of this invention.

As an alternative the compounds may be administrated with the animal feedstuff and for this purpose a concentrated feed additive or premix may be prepared for mixing with the normal animal feed.

For use as an insecticide and for treating agricultural pests the compounds are applied as sprays, dusts, pour-on formulations, emulsions and the like in accordance with standard agricultural practice.

For human use the compounds are administered as a pharmaceutically acceptable formulation in accordance with normal medical practice.

The invention is illustrated by the following Examples, in which "avermectin B2" refers to an avermectin having an OH substituent at the 23-position and a single bond at the 22–23 position, "avermectin B1" refers to an avermectin having a double bond at the 22–23 position, "avermectin B1a" is as for avermectin B1 and having a sec-butyl substituent at the 25-position. An avermectin monosaccharide is an avermectin derivative having an alpha-oleandrosyl substituent at the 13-position, the avermectins themselves having a $4^1$-(alpha-oleandrosyl)-alpha-oleandrosyl group at this position.

NMR spectra were measured using a Bruker 300 MHz spectrometer. Mass spectra were measured on a VG Mark I 7070E mass spectrometer using a sample matrix of triethylene glycol with solid sodium chloride.

EXAMPLE 1

5-Cyanomethylidene-25-cyclohexylavermectin B2

Tetra-n-butylammonium bromide (0.5 g), dimethylcyanomethylphosphonate (3.5 ml), 1,3-dimethyl-3,4,5,6-tetrahydro-2-(1H)-pyrimidinone (1 ml), methylene chloride (50 ml), and a solution of sodium hydroxide (17 g) in water (50 ml) were stirred together rapidly at 20° C. for 0.5 hours. Then the dichloromethane layer was separated and filtered through phase-separating paper into a flask containing the compound of Preparation 1 (0.5 g). The resultant solution was stirred at 20° C. for 0.5 hour. The mixture was evaporated in vacuo at 40° C. and then dissolved in methylene chloride (50 ml) and then washed with saturated ammonium chloride solution (50 ml). The organic layer was separated and dried over sodium sulphate, then filtered and evaporated in vacuo. The residue was purified by chromatography on silica gel (50 g). Elution was with a mixture of methylene chloride and methanol. The proportion of methanol was increased from 0 to 7% over 2 liters. 50 ml fractions were collected and the product identified by thin-layer chromatography. (Rf=0.3 using a solvent system of 5% methanol in methylene chloride). Final purification was achieved by reverse-phase HPLC, using a C18 Zorbax (Trademark, Dupont) column (21 mm×25 cm) eluting with a mixture of methanol and water (80:20) at a flowrate of 9 mls per minute. 4.5 ml fractions were collected and fractions 118 to 130 were combined and evaporated to yield a compound of formula (I), wherein $R^1$ is OH, $R^2$ is cyclohexyl, $R^3$ is 4'-(alpha-L-oleandrosyl)-L-oleandrosyloxy, $R^4$ is H, the 22,23 double-bond is absent, $R^6$ and $R^7$ are methyl, $R^{12}$ is CN and $R^{13}$ is H. The compound has characteristic mass and NMR spectra:

Mass spectrum (FAB): 976 (MK+). NMR spectrum (300 MHz): δ ($CDCl_3$) ppm: 6.1 (s,1H)} H-3 and H-5a. 6.12 (s,1H)}; 1.6 (s,3H, H-4a).

EXAMPLE 2

5-(Carbamoylmethylidene-25-cyclohexyl) avermectin B2

The product of Example 1 (250mg) was dissolved in methylene chloride (100 ml) and manganese dioxide (1.15 g) was added. The resulting suspension was stirred at 20° C. for 1 day. Then a further 1 g of manganese dioxide was added and stirring continued for 2 days. Then another 1 g of manganese dioxide was added to the reaction mixture and stirring continued for 1 week. The mixture was then filtered through a pad of celite and the filtrate evaporated. The residue was purified by reverse-phase HPLC, using a C18 Zorbax (Trademark, Dupont) column (21 mm×25 cm) eluting with a mixture of methanol and water (75:25) at a flowrate of 9mls/min. The relevant fractions were combined to yield a compound of formula (I), wherein $R^1$ is OH, $R^2$ is cyclohexyl, $R^3$ is 4'-(alpha-L-olendrosyl)-L-oleandrosyloxy, $R^4$ is H, the 22,23 double-bond is absent, $R^6$ and $R^7$ are methyl, $R^{12}$ is $CONH_2$ and $R^{13}$ is H. The compound has characteristic mass and NMR spectra:

Mass spectrum (FAB): 994 (MK+). NMR spectrum (300 MHz): δ ($CDCl_3$) ppm: 6.6 (s,1H)} H-3 and H-5a 6.2 (s,1H)}; 1.6 (s,3H, H-4a). 6.2 (br.s. 1H)} $NH_2$ of; 5.5 (br.s. 1H)} carbamoyl;

EXAMPLE 3

5-Cyanomethylidene-22,23-dihydroavermectin B1a monosaccharide

By the method of Example 1 the title compound was prepared from the compound of Preparation 2. Purification was achieved by column chromatography on silica gel (30 g) eluting with a mixture of ethyl acetate in methylene chloride. The proportion of ethyl acetate was increased from 0 to 40% over 2 liters. Final purification was achieved by reverse-phase HPLC, using a C-18 Zorbax (Trademark, Dupont) column (21 mm×25 cm) eluting with a mixture of methanol and water (81:19) at a flowrate of 9 mls/min. 9 ml fractions were collected. Fractions 70 to 80 were combined to yield a compound of formula (I), wherein $R^1$ is H, $R^2$ is 2-butyl, $R^3$ is L-oleandrosyloxy, $R^4$ is H, the double bond is absent, $R^6$ and $R^7$ are methyl, $R^{12}$ is CN and $R^{13}$ is H. The compound has characteristic mass and NMR spectra:

Mass spectrum (FAB): 790 (MK+). NMR spectrum (300MHz): δ ($CDCl_3$) ppm: 6.1 (s,1H)} H-3 and H-5a. 6.12 (s,1H)}; 1.55 (s,3H, H-4a).

EXAMPLE 4

5-Methylidene-22,23-dihydroavermectin B1a monosaccharide

To a stirred solution of methyl triphenylphosphonium bromide (430mg) in dry tetrahydrofuran at 0° C. under nitrogen was added a solution of butyl lithium in hexanes (1.6M, 0.75ml ). The suspension was stirred for 15 minutes at 0° C., then the compound of Preparation 2 (140 mg) in dry tetrahydrofuran (10 ml) was added. The cooling bath was removed and the stirred mixture allowed to warm to 20° C. After stirring at this temperature for 1 hour the reaction mixture was added to saturated ammonium chloride solution (50ml) and extracted with methylene chloride. The organic layer was separated and dried over sodium sulphate, then filtered and evaporated. The residue was purified by reverse-phase HPLC. The column used by a C18 Zorbax (Trademark, Dupont), (21 mm×25 cm), eluting with a mixture of methanol and water (86:14) at a flow rate of 9 mls/min. 9ml fractions were taken and fractions 58 to 64 were combined and evaporated to yield the compound of formula (I) wherein $R^1$ is H, $R^2$ is 2-butyl, $R^3$ is L-oleandrosyloxy, $R^4$ is H, the double bond is absent, $R^6$ and $R^7$ are methyl, $R^{12}$ and $R^{13}$ are H. The compound has characteristic mass and NMR spectra:

Mass spectrum (FAB): 749 (MNa+). NMR spectrum (300MHz) δ ($CDCl_3$) ppm: 5.55 (br.s., 2H, H-5a). 1.9 (br.s., 3H, H-4a).

EXAMPLE 5

5-Methylidene-25-cyclohexyl-22,23-dihydroavermectin B1 monosaccharide

By the method of Example 4 the title compound was prepared from the compound of Preparation 3. Purification was achieved by column chromatography on silica gel (150 g); eluting with hexane, then methylene chloride, then ethyl acetate. Relevant fractions were combined to yield, on evaporation, 760 mg of crude material. Further purification was achieved by reverse-phase HPLC on a Dynamax C-18 (Trademark, Rainin) column, (41.4 mm×25 cm) eluting with a mixture of methanol and water (88:12) at a flowrate of 40 mls/min. Fractions 29 to 34 were combined and evaporated to yield 139 mg of a compound of formula (I) wherein $R^1$ is H, $R^2$ is cyclohexyl, $R^3$ is L-oleandrosyloxy, $R^4$ is H, the double bond is absent, $R^6$ and $R^7$ are methyl, $R^{12}$ and $R^{13}$ are H. The compound has characteristic mass and NMR spectra:

Mass spectrum (FAB): 775 (MNa+). NMR spectrum (300MHz): δ ($CDCl_3$) ppm: 5.57 (br.s., 2H, H-5a). 1.95 (br.s., 3H, H-4a).

EXAMPLE 6

5-Methylidene-25-cyclohexylavermectin B2

By the method of Example 4, the title compound was prepared from the compound of Preparation 1. Following silica gel chromatography, 80 mg of a crude product was isolated. This was further purified by reverse-phase HPLC on a Dynamax C-18 (Trademark, Rainin) column, (41.4 mm×25 cm) eluting with a mixture of methanol and water (85:15) at a flowrate of 40 mls/min. 30 ml fractions were collected, and fractions 35 to 44 were combined and evaporated to yield the compound of formula (I), (130 mg), wherein $R^1$ is OH, $R^2$ is cyclohexyl, $R^3$ is 4'-(alpha-L-oleandrosyl)-L-oleandrosyloxy, $R^4$ is H, the 22,23 double bond is absent, $R^6$ and $R^7$ are methyl and $R^{12}$ and $R^{13}$ are H. The compound has characteristic mass and NMR spectra:

Mass spectrum (FAB): 930 ($MNH_4$+). NMR spectrum (300 MHz): δ ($CDCl_3$) ppm: 5.55 (br.s., 2H, H-5a). 1.9 (br.s., 3H, H-4a).

EXAMPLE 7

5-Ethylidene-25-cyclohexylavermectin B2

The title compound was prepared by the method of Example 6, except that ethyl triphenylphosphonium bromide was used instead of methyl triphenylphosphonium bromide. The product was purified by reverse-phase HPLC using a C18 Zorbax (Trademark, Dupont) column (21 mm×25 cm) eluting with a mixture of methanol and water (84:16) at a flowrate of 9 mls/min. 9 ml fractions were collected and fractions 86 to 90 were combined and evaporated to yield a compound of formula (I) wherein $R^1$ is OH, $R^2$ is cyclohexyl, $R^3$ is 4'-(alpha-L-oleandrosyl)-L-oleandrosyloxy, $R^4$ is H, the 22,23 double bond is absent, $R^6$ and $R^7$ are methyl, $R^{12}$ is H and $R^{13}$ is methyl. The compound has characteristic mass and NMR spectra:

Mass spectrum (FAB): 949 (MNa+). NMR spectrum (300 MHz): δ ($CDCl_3$) ppm: 5.55 (br.s., 1H, H-5a). 2.15 (br.s., 3H, H-5b). 2.0 (br.s., 3H, H-4a).

PREPARATION 1

5-Keto25cyclohexylavermectin B2

To a suspension of manganese dioxide (3 g) in diethyl ether (50 ml) was added 25cyclohexylavermectin B2 (2 g), obtained as described in EP-A-214731. The mixture was stirred for 1 day, and a further portion of manganese dioxide (3 g) was added. After stirring for a second day at 20° C. a third portion of manganese dioxide was added and the mixture stirred for a third day. The manganese dioxide was then removed by filtration through Celite and the filtrate was evaporated to give 0.6 g of the title compound which has characteristic mass and NMR spectra:

Mass spectrum (FAB): 937 (MNa+). NMR spectrum (300 MHz): δ (CDCl$_3$) ppm: 6.6 (br.s., 1H, H-3). 1.9 (br.s., 3H, H4a).

PREPARATION 2

5-Keto-22,23-dihydroavermectin B1a monosaccharide

By the method of Preparation 1, the title compound was prepared from 25-(2-butyl)-22,23-dihydroavermectin B1a monosaccharide obtained as described in U.S. Pat. No. -4,199,569.

PREPARATION 3

5-Keto-25cyclohexyl-22,23-dihydroavermectin B1 monosaccharide

25-Cyclohexylavermectin B1 (9.9 g) was dissolved in toluene (1 liter) and Wilkinson's catalyst (tristriphenylphosphine rhodium (I) chloride) (9.25 g) was added. The solution was hydrogenated on a large Parr shaker at room temperature at 50 psi hydrogen pressure. After 3 hours the reaction vessel was depressurised and allowed to stand for 12 hours before addition of a further portion of catalyst (5 g) and hydrogenated as before for a further 2 hours after which no starting material remained. The solution was filtered, evaporated to dryness under vacuum and the residue chromatographed on silica eluting with methylene chloride then methylene chloride:methanol 9:1. The crude product was then chromatographed again on silica (200 g) eluting with methylene chloride:methanol 19:1 to give after evaporation of the solvent under vacuum impure 22,23-dihydro-25-cyclohexylavermectin B1 as a brown foam (10 g). This material was dissolved in a mixture of isopropanol (200 ml) and sulphuric acid (2 ml ) and the brown solution was stirred at room temperature for 15 hours then poured into a mixture of ice and water (500 ml) and extracted with methylene chloride (3×200 ml ). The organic layer was washed with saturated potassium hydrogen carbonate solution (100 ml), water (2×50 ml ) dried over anhydrous magnesium sulphate and evaporated under vacuum to give a crude gum which was chromatographed on silica eluting with methylene chloride then methylene chloride:ethyl acetate 2:1 to give 22,23-dihydro-25-cyclohexylavermectin B1 monosaccharide. This compound was dissolved in anhydrous diethyl ether and the solution stirred with manganese dioxide to yield the title product.

We claim:

1. A compound of formula (I):

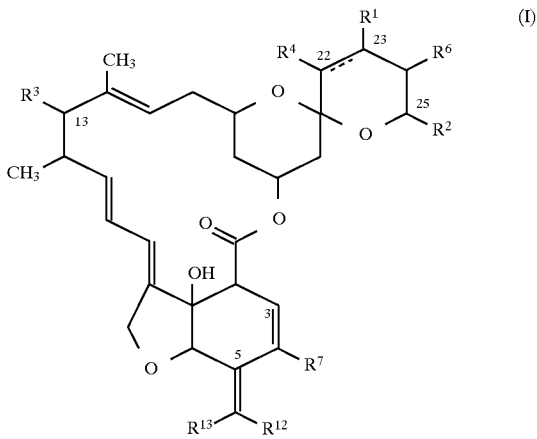

wherein the broken line represents an optional bond, $R^1$ and $R^4$ being absent when this bond is present, $R^1$ and $R^4$ are independently H or $OR^{14}$ where $R^4$ is H, $C_1$–$C_8$ alkyl, $C_2$–$C_8$ alkenyl, aralkyl, $C_2$–$C_8$ alkanoyl, $C_3$–$C_8$ alkenoyl, aralkanoyl, aroyl or carbamoyl;

$R^2$ is:
(a) an alpha-branched $C_3$–$C_8$ alkyl, alkenyl, alkoxy-alkyl, or alkylthioalkyl group; an alpha-branched $C_4$–$C_8$ alkynyl group; a ($C_5$–$C_8$)cycloalkyl-alkyl group wherein the alkyl group is an alpha-branched $C_2$–$C_5$ alkyl group; a $C_3$–$C_8$ cycloalkyl or $C_5$–$C_8$ cycloalkenyl group, either of which is optionally substituted by methylene or one or more $C_1$–$C_4$ alkyl groups or halo atoms; or a 3 to 6 membered oxygen or sulphur containing heterocyclic ring which is saturated, or fully or partially unsaturated and which is optionally substituted by one or more $C_1$–$C_4$ alkyl groups or halo atoms; or
(b) a group of the formula —$CH_2R^8$ wherein $R^8$ is H, $C_1$–$C_8$ alkyl, $C_2$–$C_8$ alkenyl, $C_2$–$C_8$ alkynyl, alkoxy-alkyl or alkylthioalkyl containing from 1 to 6 carbon atoms in each alkyl or alkoxy group, wherein any of said alkyl, alkoxy, alkenyl or alkynyl groups are optionally substituted by one or more halo atoms; or $R^8$ is a $C_3$–$C_8$ cycloalkyl or $C_5$–$C_8$ cycloalkenyl group, either of which is optionally substituted by methylene or one or more $C_1$–$C_4$ alkyl groups or halo atoms; or $R^8$ is a 3 to 6 membered oxygen or sulphur containing heterocyclic ring which is be saturated, or fully or partially unsaturated and which is optionally substituted by one or more $C_1$–$C_4$ alkyl groups or halo atoms; or $R^8$ is a group of the formula $SR^9$ wherein $R^9$ is $C_1$–$C_8$ alkyl, $C_2$–$C_8$ alkenyl, $C_3$–$C_8$ alkynyl, $C_3$–$C_8$ cycloalkyl, $C_5$–$C_8$ cycloalkenyl, phenyl or substituted phenyl wherein the substituent is $C_1$–$C_4$ alkyl, $C_1$–$C_4$ alkoxy or halo; or $R^8$ is a 3 to 6 membered oxygen or sulphur containing heterocyclic ring which is saturated, or fully or partially unsaturated and which is optionally substituted by one or more $C_1$–$C_4$ alkyl groups or halo atoms; or
(c) a $C_1$–$C_6$ alkyl group substituted by one oxo or one or more hydroxy groups or by a single oxygen atom on two adjacent carbon atoms forming an oxirane ring, or $R^2$ is a $C_1$–$C_5$ alkyl group substituted by a ($C_1$–$C_6$) alkoxycarbonyl group, said substituents on $R_2$ being attached to either or both of a terminal carbon atom and a carbon atom adjacent a terminal carbon atom of $R^2$; or (d) =$CH_2$ or a group of the formula:

$$-(X)-\underset{|}{\overset{R^{10}}{C}}=CHR^{11}$$

wherein $R^{10}$ and $R^{11}$ are both H; $R^{10}$ is H and $R^{11}$ is $C_1$–$C_3$ alkyl, or one of $R^{10}$ and $R^{11}$ is H and the other is phenyl, heteroaryl, $C_2$–$C_6$ alkoxycarbonyl or substituted phenyl or heteroaryl wherein said substituent is fluorine, chlorine, $C_1$–$C_4$ alkyl, $C_1$–$C_4$ alkoxy, $C_1$–$C_4$ alkylthio, hydroxy ($C_1$–$C_4$)alkyl, cyano, aminosulphonyl, $C_2C_6$ alkanoyl, $C_2$–$C_6$ alkoxycarbonyl, nitro, trifluoromethyl, trifluoromethoxy, amino or mono or di($C_1$–$C_4$) alkylamino; and X is a direct bond or is an alkylene group having from 2 to 6 carbon atoms which is straight or branched-chain; or (e) phenyl which may optionally be substituted with at least one substituent selected from $C_1$–$C_4$ alkyl, $C_1$–$C_4$ alkylthio groups, halo atoms, trifluoromethyl, and cyano;

or $R^2$ is a group of formula (II):

[structure with $(CH_2)_a$, $(CH_2)_b$, $(CH_2)_c$, $(CH_2)_d$ and Z]

wherein Z is O, S or —$CH_2$— and a, b, c and d are each independently 0, 1 or 2, the sum of a, b, c and d not exceeding 5;

$R^6$ is H or $C_1$–$C_6$ alkyl;

$R^7$ is $CH_3$, —$CH_2$—$OR^{14}$ where $R^{14}$ is as defined above, or —$CH_2X$ where X is a halogen atom; and $R^3$ is a group of formula:

[two sugar structures with $R^5$, $H_3C$, $H_3CO$, at positions 4', 4"]

or

[single sugar structure with $R^5$, $H_3C$, $H_3CO$, at position 4']

wherein $R^5$ is attached to C-4" or C-4' by a single bond and is hydrogen, halo, hydroxy, $C_2$–$C_9$ alkanoyloxy, $C_3$–$C_9$ alkenoyloxy, aroyloxy, $C_1$–$C_8$ alkoxy, amino, N-($C_1$–$C_8$) alkylamino, N,N-di($C_1$–$C_9$)-alkylamino, N-($C_2$–$C_9$) alkanoylamino, or N,N-di($C_2$–$C_9$)alkanoylamino;

or $R^5$ is attached to C-4" or C-4' by a double bond and is oxo, optionally substituted oximino, semicarbazido, N-($C_1$–$C_4$)alkylsemicarbazono, N,N-di($C_1$–$C_4$) alkylsemicarbazono, ($C_1$–$C_4$)alkylbenzoylhydrazono, and $R^{12}$ and $R^{13}$ are independently H, CN, $CONH_2$, $C_1$–$C_6$ alkyl or aryl optionally substituted with at least one halo, OH, $C_1$–$C_6$ alkoxy or $C_1$–$C_6$ alkylthio group.

2. A compound according to claim 1, in which $R^4$ is H and $R^1$ is OH.

3. A compound according to claim 1 in which $R^2$ is isopropyl, sec-butyl or cyclohexyl.

4. A compound of claim 1 in which $R^5$ is —OH.

5. A compound of claim 1 in which one of $R^{12}$ and $R^{13}$ is H and the other is H, methyl, cyano or carbamoyl.

6. A compound according to claim 1 which is:

5-cyanomethylidene-25-cyclohexyl avermectin B2;

5-carbamoylmethylidene-25-cyclohexyl avermectin B2;

5-cyanomethylidene-22,23-dihydroavermectin B1a monosaccharide;

5-methylidene-22,23-dihydroavermectin B1a monosaccharide;

5-methylidene-25-cyclohexyl-22,23-dihydroavermectin B1 monosaccharide;

5-methylidene25-cyclohexylavermectin B2; or 5-ethylidene-25-cyclohexylavermectin B2.

7. A pharmaceutical composition comprising an effective amount of a compound of claim 1 and a pharmaceutically acceptable carrier or diluent.

8. A method of treating parasitic infections in a mammal comprising administering to said mammal an antiparasitic effective amount of a compound of claim 1.

9. A method of preventing parasitic infections in a mammal comprising administering to said mammal an antiparasitic effective amount of a compound of claim 1.

10. A method of making a compound of formula (I) as defined in claim 1 which comprises reacting a compound of formula (II),

[avermectin macrocyclic structure with labeled positions $R^1$, $R^2$, $R^3$, $R^4$, $R^7$, 3, 5, 13, 22, 23, 25, $CH_3$]

wherein $R^1$, $R^2$, $R^3$, $R^4$, $R^6$ and $R^7$ are as defined in claim 1 with a compound of formula $R^{13}R^{12}C$=$PPh_3$ where $R^{12}$ and $R^{13}$ are as defined in claim 1 and Ph is phenyl.

11. A method according to claim 10 in which the reaction takes place in an inert organic solvent at a temperature from −100° C. to 0° C.

12. A method of claim 11 in which $R^{12}$ or $R^{13}$ is cyano and the cyano group is subsequently converted to a carbamoyl group by hydrolysis.

13. A method according to claim 10, in which $R^{12}$ or $R^{13}$ is cyano and the cyano group is subsequently converted to a carbamoyl group by hydrolysis.

* * * * *